(12) United States Patent
Shkolnikov et al.

(10) Patent No.: US 10,888,866 B2
(45) Date of Patent: Jan. 12, 2021

(54) LIQUID DIRECTING SAMPLE CONTAINER

(71) Applicant: Hewlett-Packard Development Company, L.P., Spring, TX (US)

(72) Inventors: Viktor Shkolnikov, Palo Alto, CA (US); Anita Rogacs, San Diego, CA (US)

(73) Assignee: Hewlett-Packard Development Company, L.P., Spring, TX (US)

(*) Notice: Subject to any disclaimer, the term of this patent is extended or adjusted under 35 U.S.C. 154(b) by 120 days.

(21) Appl. No.: 15/772,511

(22) PCT Filed: Feb. 29, 2016

(86) PCT No.: PCT/US2016/020104
§ 371 (c)(1),
(2) Date: Apr. 30, 2018

(87) PCT Pub. No.: WO2017/151098
PCT Pub. Date: Sep. 8, 2017

(65) Prior Publication Data
US 2019/0076839 A1    Mar. 14, 2019

(51) Int. Cl.
*B01L 3/00* (2006.01)
*C12M 1/00* (2006.01)
(Continued)

(52) U.S. Cl.
CPC ........... *B01L 3/5085* (2013.01); *B01L 3/5025* (2013.01); *C12M 23/02* (2013.01); *G01N 21/03* (2013.01);
(Continued)

(58) Field of Classification Search
CPC ................. B01L 3/5085; B01L 3/5025; B01L 2400/0487; B01L 2400/0406;
(Continued)

(56) References Cited

U.S. PATENT DOCUMENTS 7,326,385 B2    2/2008 Everett
9,206,384 B2    12/2015 Lee et al.
(Continued)

FOREIGN PATENT DOCUMENTS

WO    WO-2005/060678 A2    7/2005
WO    WO-2010/033267 A2    3/2010
(Continued)

OTHER PUBLICATIONS

Abell, J.L. et al., "Fabrication and Characterization of a Multiwell Array SERS Chip with Biological Applications", Biosensors and Bioelectronics, vol. 24, Issue 12, Aug. 15, 2009, p. 3663-3670. http://www.sciencedirect.com/science/articie/pii/S0956566309003121.
(Continued)

*Primary Examiner* — Benjamin R Whatley
*Assistant Examiner* — Jean Caraballo-Leon
(74) *Attorney, Agent, or Firm* — Rathe Lindenbaum LLP

(57) ABSTRACT

A liquid directing sample container includes a well. The well has sides and a floor. The sides having a non-circular profile having an interior angle that, at a target location within the well, is smaller than other interior angles of the profile to wick liquid towards the target location. The floor is sloped downward towards the target location.

15 Claims, 9 Drawing Sheets

(51) Int. Cl.
*G01N 21/03* (2006.01)
*G01N 21/11* (2006.01)
*G01N 21/65* (2006.01)

(52) U.S. Cl.
CPC ......... *G01N 21/0317* (2013.01); *G01N 21/11* (2013.01); *G01N 21/658* (2013.01); *B01L 2300/0645* (2013.01); *B01L 2300/0654* (2013.01); *B01L 2300/0829* (2013.01); *B01L 2300/0851* (2013.01); *B01L 2300/1827* (2013.01); *B01L 2400/0406* (2013.01); *B01L 2400/0487* (2013.01)

(58) Field of Classification Search
CPC ..... B01L 2300/1827; B01L 2300/0851; B01L 2300/0829; B01L 2300/0654; B01L 2300/0645; G01N 21/03; G01N 21/0317; G01N 21/658; G01N 21/11; C12M 23/02

See application file for complete search history.

(56) References Cited

U.S. PATENT DOCUMENTS

| | | |
|---|---|---|
| 2003/0215940 A1 | 11/2003 | Lacey et al. |
| 2006/0006068 A1 | 1/2006 | Desmond et al. |
| 2010/0029000 A1 | 2/2010 | Zhong et al. |
| 2010/0230284 A1* | 9/2010 | Stephenson ............. B01L 3/502 204/403.01 |
| 2012/0190032 A1 | 7/2012 | Ness et al. |
| 2013/0065795 A1 | 3/2013 | Allbritton et al. |
| 2013/0130369 A1* | 5/2013 | Wilson ................... G16B 99/00 435/289.1 |
| 2014/0196550 A1 | 7/2014 | Chernomorsky et al. |
| 2014/0302611 A1 | 10/2014 | Orning et al. |
| 2016/0040112 A1* | 2/2016 | Coppeta ................. C12M 27/00 435/325 |

FOREIGN PATENT DOCUMENTS

| | | |
|---|---|---|
| WO | WO-2014/153092 A1 | 9/2014 |
| WO | WO-2015135840 | 9/2015 |

OTHER PUBLICATIONS

International Search Report and Written Opinion dated Oct. 20, 2016, PCT Patent Application No. PCT/US2016/020104, filed Feb. 29, 2016, Korean Intellectual Property Office.

* cited by examiner

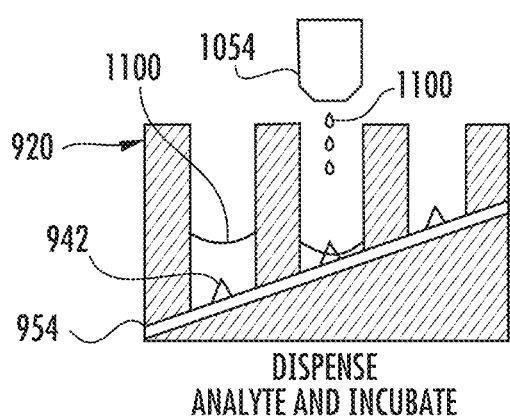
FIG. 18 — DISPENSE ANALYTE AND INCUBATE
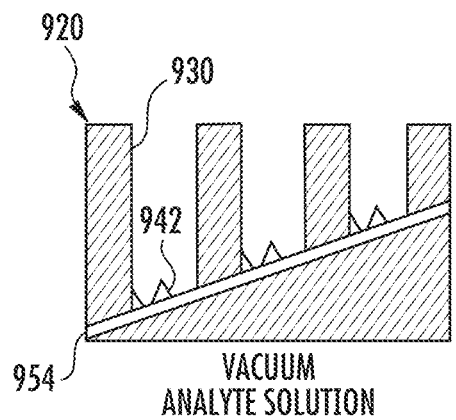
FIG. 19 — VACUUM ANALYTE SOLUTION
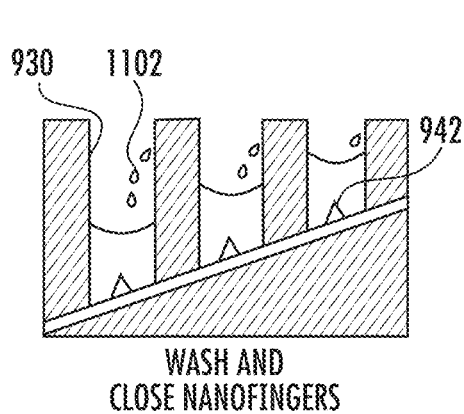
FIG. 20 — WASH AND CLOSE NANOFINGERS
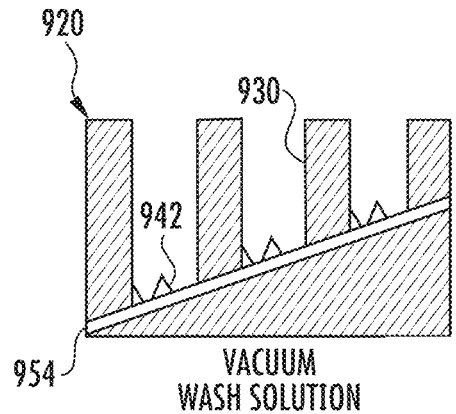
FIG. 21 — VACUUM WASH SOLUTION
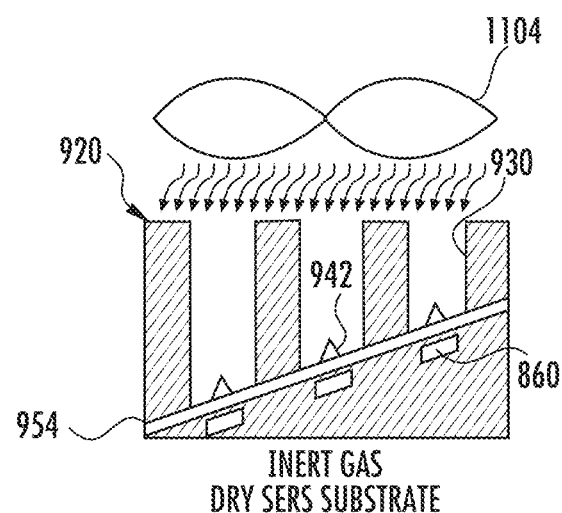
FIG. 22 — INERT GAS DRY SERS SUBSTRATE
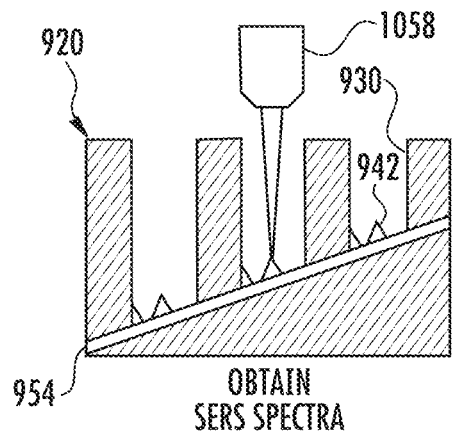
FIG. 23 — OBTAIN SERS SPECTRA

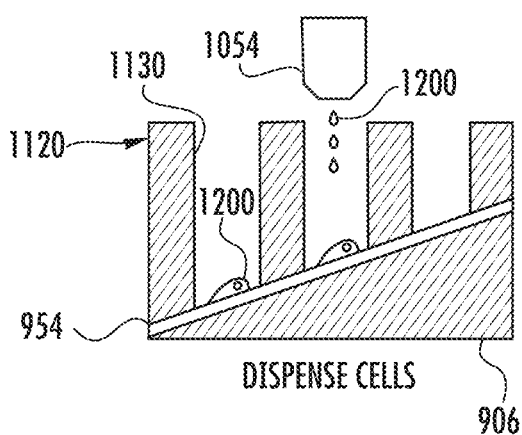
FIG. 24 DISPENSE CELLS
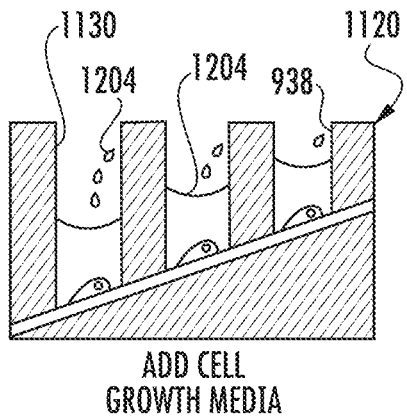
FIG. 25 ADD CELL GROWTH MEDIA
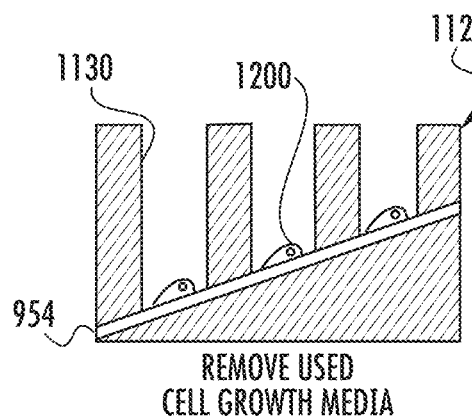
FIG. 26 REMOVE USED CELL GROWTH MEDIA
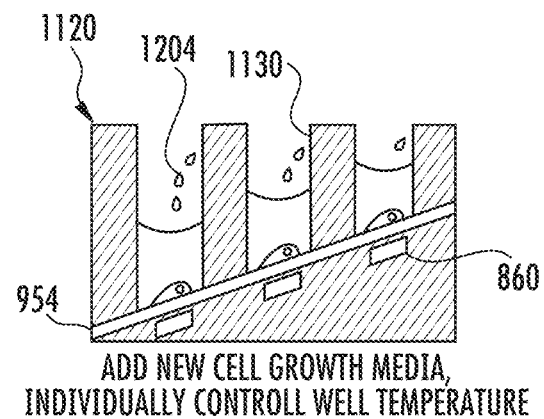
FIG. 27 ADD NEW CELL GROWTH MEDIA, INDIVIDUALLY CONTROLL WELL TEMPERATURE
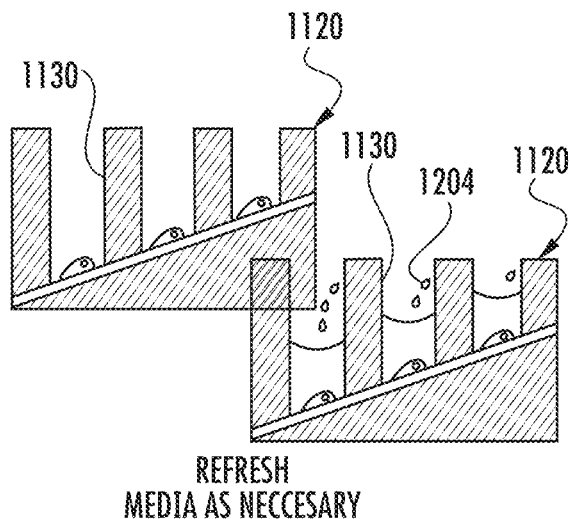
FIG. 28 REFRESH MEDIA AS NECCESARY
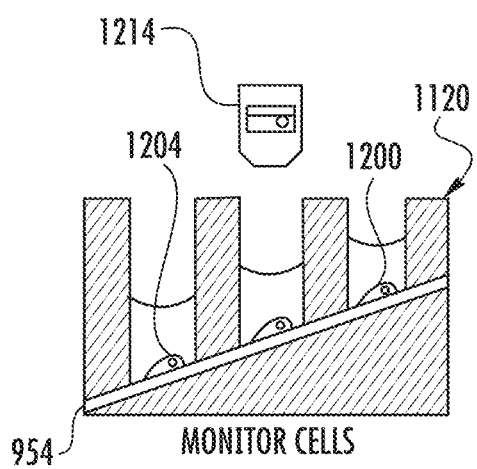
FIG. 29 MONITOR CELLS

LIQUID DIRECTING SAMPLE CONTAINER

CLAIM FOR PRIORITY

The present application is a national stage filing under 35 U.S.C. § 371 of PCT application number PCT/US2016/020104, having an international filing date of Feb. 29, 2016, the disclosure of which is hereby incorporated by reference in its entirety.

BACKGROUND

Well plates often include an array of wells to contain samples. Sometimes the samples comprise cultures that are being grown. Sometimes the samples comprise analytes to be tested.

BRIEF DESCRIPTION OF THE DRAWINGS

FIG. 2 is a sectional view of an example liquid directing sample container.

FIGS. 18-23 are sectional views of an example sample preparation and sensing method carried out with a portion of the liquid directing sample container of FIG. 16.

FIGS. 24-29 are sectional views of an example cell growth method carried out with an example liquid directing sample container.

DETAILED DESCRIPTION OF EXAMPLES

Many processes that utilize well plates to contain liquid, such as analyte samples or cell culture growth media, involve manipulation of the liquid within the individual wells. For example, in many processes, the well plates are centrifuged before incubation to positionally direct the liquid within the well.

In some processes, the liquid is removed from the well. For example, preparation of an analyte sample for testing may involve exchanging the sample within the well plate. Likewise, growing a culture within a well plate also may involve exchanging liquids within the well plate. With many existing well plates, it may be difficult to remove liquid from the individual wells of the well plate. Incomplete removal of liquid from the individual wells may raise contamination issues. For example, when testing an analyte, the practice is sometimes to remove the original sample solution and apply a rinsing solvent or wash solution to a sensor within the well. Any of the original sample solution remaining in the well might otherwise contaminate the wash solution, reducing the efficiency of the wash and possibly involving additional wash steps. When growing a culture in a well, the practice is sometimes to replace the liquid growth medium after nutrients, growth promoters and the like in the old growth medium have been exhausted. Any of the original growth medium remaining in the well may introduce waste and may introduce unwanted cellular signaling molecules or old cells that may provide unwanted information.

Figure 1:
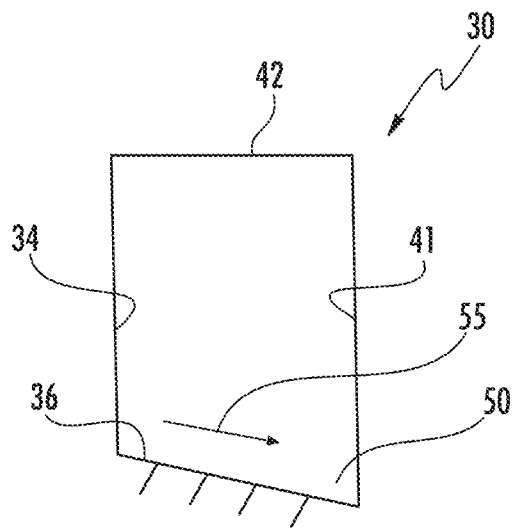
FIG. 1 is a sectional view of an example liquid directing sample container.
Figure 1A:
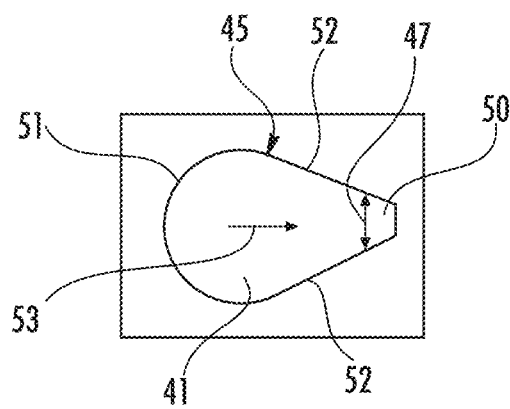

FIGS. 1 and 1A schematically illustrate an example liquid directing sample container. As will be described hereafter, the liquid directing sample container has an interior that directs and influences the movement of liquid towards a target location within the interior. In some implementations, by influencing or biasing movement of fluid within the interior of the well towards a target location, the container may reduce or eliminate the time for centrifuging the liquid. In some implementations, by influencing or biasing movement of fluid within the well towards a target location that is adjacent to a discharge port, the container may facilitate enhanced removal of liquids from the individual wells and may reduce contamination concerns. As a result, the container facilitates more efficient processing of samples, whether to prepare an analyte sample for testing or to grow a culture for testing.

As shown by FIG. 1, the container includes a well 30 to contain a liquid sample. Well 30 comprises sides 34 and floor 36. Sides 34 rise up from floor 36 in an upward direction, parallel to one another, to form an interior 41 having a mouth 42.

As shown by FIG. 1A, sides 34 have a non-cylindrical profile and a non-circular cross-section. Sides 34 have a profile 45 with an interior angle 47 that, at a target location within the well 30, is smaller than other interior angles of the profile 45. In the example illustrated, interior angle 47 is smaller than all other interior angles of profile 45. In contrast to angle 47, remaining interior angles of well 30 are either curved or rounded and greater than 90°. As a result, liquid is less likely to be held up or retained by capillary action between or within corners or acute angles. At the same time, capillary action assists in wicking liquid towards the target location 50. In one implementation, the target location 50 may be a predetermined region in the interior 41 of well 30 to which liquid is to be moved, leaving less liquid or no liquid in other portions of the interior 41 of well 30. In some implementations, the wicking of liquid towards target location 50 may reduce or eliminate any centrifuging step of a process.

In the example illustrated, profile 45 is illustrated as having a tear-drop shape, having a curved or rounded portion 51 opposite to target location 50 and two converging segments 52 extending from rounded portion 51 towards target location 50. As a result, liquid is whipped through capillary forces within interior 41 in the direction indicated by arrow 53. As will be described hereafter, in other implementations, target location 50 may be provided at other portions within the interior of well 30. In other implementations, profile 45 may have other shapes.

As shown by FIG. 1, floor 36 extends at the bottom of well 30. Floor 36 is sloped, inclined or ramped in a downward direction (away from mouth 42) towards target location 50. In the example illustrated, floor 36 has a constant non-zero angle slope with respect to a horizontal plane. In one implementation, floor 36 is sloped at a nonzero angle of less than 90° with respect to the horizontal direction or plane. As a result, sloped floor 36 further influences and directs the movement of fluid within interior 41 of well 30. Under the influence of gravity, liquid within well 30 is biased towards target location 50 as indicated by arrow 55.

Although well 30 is illustrated as having sloped floor 36, in other implementations, well 30 may have a differently sloped floor, such as the floor described hereafter with respect to well 130б or other floor profiles. Although the container is illustrated as having a single well 30, in other implementations, the container may have multiple wells 30, such as a two dimensional array of such wells 30.

Figure 2:
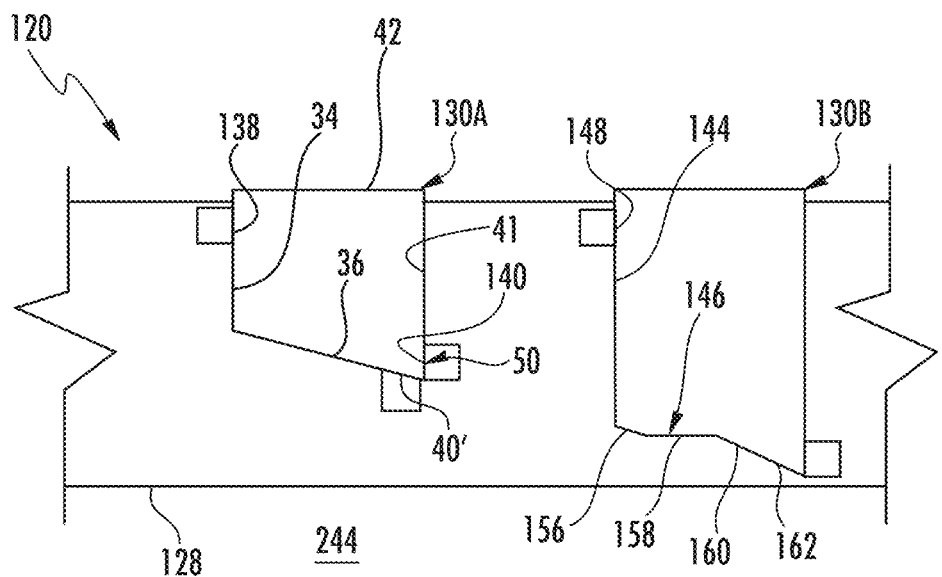
FIG. 2 is a top view of the example liquid directing sample container of FIG. 1.
Figure 3:
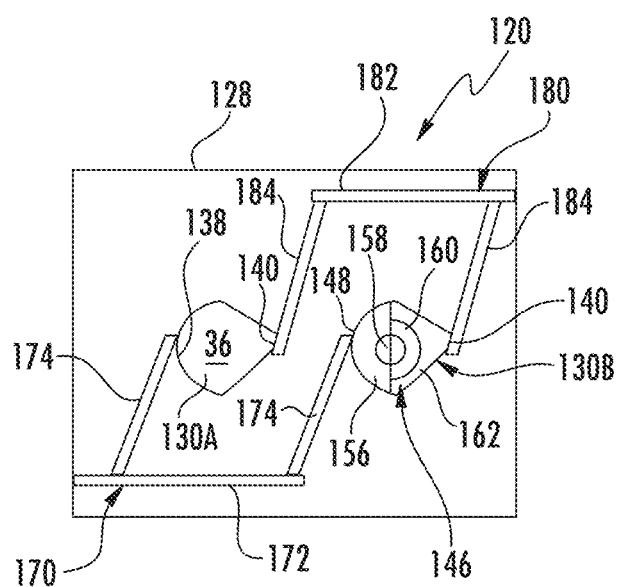
FIG. 3 is a top view of the example liquid directing sample container of FIG. 2.

FIGS. 2 and 3 schematically illustrate liquid directing sample container 120, which may be another implementation of the container depicted in FIGS. 1 and 1A. Container 120 comprises well plate 128, wells 130A, 130B (collectively referred to as wells 130), dispense passage 170 and discharge passage 180. Well plate 128 comprises a structure in which wells 130 are formed. In one implementation, wells 130 are molded into well plate 128. In another implementation, wells 130 are formed within well plate 128 through material removal processes. In one implementation, well plate 128 comprises a polymer. In other implementations, well plate 128 comprises and/or is formed from other materials such as a silicon-based material.

Wells 130 are each to contain a liquid sample. Well 130A is similar to well 30 except that well 130A additionally comprises a dispense port or inlet 138 through which liquid may be dispensed into interior 41 of well 130A and discharge port 140. Those components or elements of well 130A which correspond to components or elements of well 30 are numbered similarly.

In the example illustrated, inlet 138 extends through sides 34 of well 130A on an opposite side of well 130A as target location 50 and discharge port 140. In the example illustrated, inlet 138 is located at a height spaced above floor 36 proximate to mouth 42. In other implementations, inlet 138 may be located adjacent to floor 36 at an upper end of the sloped floor 36.

Discharge port 140 comprises an opening through the sides 34 of well 130A at the bottom of the sloped floor 36, adjacent target location 50. As illustrated by broken lines, in other embodiments, well 130A may alternatively have an alternative discharge port 40' extending through the lower end of floor 36. Because discharge port 140 is located at a lower end of the sloped floor 36, floor 36, with the assistance of gravity, facilitates movement of liquid within the interior 41 of well 130A towards discharge port 140.

Well 130B is similar to well 130A except that well 130B comprises floor 146 in place of floor 36. Well 130B is similar to well 130A except that well 130B provides different flow characteristics for the sample or contents of well 130B due to the different profile of its floor 146. Those components or elements of well 130B which correspond to components or elements of well 130A are numbered similarly.

Floor 146, like floor 36 of well 130A, is sloped towards discharge port 140. In the example illustrated, floor 146 has a non-uniform sloping angle within well 130B. In the example illustrated, floor 146 comprises sloped portions 156, 158, 160 and 162. Sloped portion 158 is horizontal or level, providing a level surface upon which a culture or analyte testing structure may rest. Portion 156 extends along sides 34 and is angled to direct liquid, under the force of gravity, towards portion 158. Portion 160 extends from portion 158 and is sloped to direct liquid away from portion 158 towards portion 162. Portion 162 has a sloped angle greater than portion 160 and greater than portion 156 to accelerate the flow of liquid towards the target location 50 and discharge port 140. In other implementations, floor 146 may have a greater or fewer of such differently sloped portions. In other implementations, the different slope portions of floor 146 may have other slopes or inclinations. In some implementations, level portion 158 of floor 146 may be omitted and replaced with a sloped portion.

Dispense passage 170 comprises a fluid conduit or passage formed within well plate 128 and connected to each of inlets 138 and 148 of wells 130A and 130B, respectively. Dispense passage 170 comprises a main portion 172 and branches 174. Main portion 172 extends to an exterior of well plate 128 for releasable connection to an external liquid source, such as a source of a sample, a source of a rinsing solvent or a source of a growth medium. For purposes of this disclosure, the term "releasably" or "removably" with respect to an attachment or coupling of two structures means that the two structures may be repeatedly connected and disconnected to and from one another without material damage to either of the two structures or their functioning. The source may selectively supply liquid, through the use of valves or the like, through passage via main portion 172 into each of wells 130. Branches 174 extend from main portion 172. In the example illustrated, branches 174 are sloped or angled downwardly towards inlets 138, 148 to further assist the flow of liquid to wells 130 under the force of gravity.

Discharge passage 180 comprises a fluid conduit or passage formed within well plate 128 and connected to each of discharge ports 140, 50 of wells 130A and 130B, respectively. Discharge passage 180 comprises a main portion 182 and branches 184. Main portion 182 extends to an exterior of well plate 128 for releasable connection to a discharge destination. In one implementation, main portion 182 extends to an exterior of well plate 128 for releasable connection to a pump to assist in withdrawing liquid from wells 130. In one implementation, main portion 182 is connectable to a pneumatic pump which is operable in two modes: a first mode pressurizing discharge passage 180 to inhibit liquid from flowing into discharge passage 180, such as when liquid is being dispensed into wells 130; and a second mode in which a negative pressure or vacuum is created in discharge passage 180 to assist in withdrawing liquid from wells 130. In yet other implementations, valves or other mechanisms may be used to selectively opening close discharge ports 140, 50.

Branches 184 extend from main portion 182. In the example illustrated, branches 184 are sloped or angled downwardly away from outlets or ports 140 to further assist the flow of liquid out of wells 130 under the force of gravity.

Although wells 130 are each illustrated as comprising a single inlet 138, 148 and a single discharge port 140, in another implementation, wells 130 may include additional inlets 138, 148 and/or additional discharge ports 140, 140' at the lowermost ends of the respective floors 36, 146. Although wells 130 are illustrated as having profile 45, in other implementations, wells 130 may have a cylindrical profile with a circular cross section shape. Although container 120 is illustrated as comprising two spaced wells, in other implementations, container 120 may include additional wells. For example, in some implementations, container 120 may comprise a two-dimensional array of wells 130.

Figure 4:
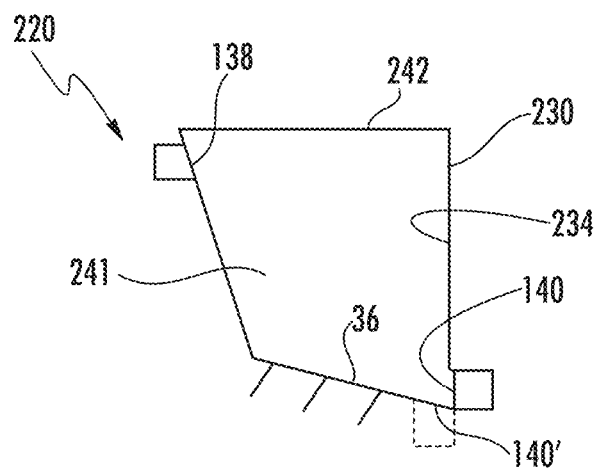
FIG. 4 is a sectional view of an example liquid directing sample container.
Figure 5:
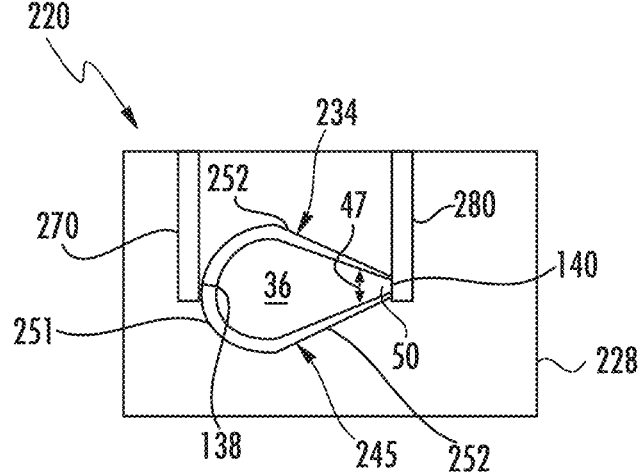
FIG. 5 is a top view of the example liquid directing sample container of FIG. 4.

FIGS. 4 and 5 illustrate liquid directing sample container 220, another example of the liquid directing sample container or liquid directing sample container 120 described above. FIGS. 4 and 5 illustrate an individual well 230 of container 220. FIG. 5 illustrates well 230 provided in an example well plate 228 and further associated with an example dispense passage 270 and with an example discharge passage 280. Dispense passage 270 is in connection with inlet 138 to supply liquid to the interior 241 of well 230. Discharge passage 280 includes a conduit in connection with discharge port 140 through which liquid is withdrawn from interior 241 of well 230. As described above, discharge port 140 may be selectively opened and closed by a valve or by the application of positive pneumatic pressure (to close) or negative pneumatic pressure (to open) from a pneumatic pump.

Well 230 is similar to well 130A described above except that well 230 comprises sides 234. Sides 234 rise up from floor 36 to form a mouth 242 and an interior 241. Sides 234 are inclined or sloped, funneling from a larger area to a smaller area as such sides 234 approach floor 36. In the example illustrated, sides 234 converge towards target location 50 and the smallest angle 47 along curved portion 51 in regions opposite to target location 50. Sides 234 further converge towards one another as sides 234 approach target location 50 and discharge port 140. As a result, sides 234 provide well 230 with a funnel-shape, providing a larger mouth 242 for depositing liquids into interior 241 and further directing or biasing the flow of liquid towards target location 50 and discharge port 140.

Similar to the sides 34 of wells 30 and 130 described above, sides 234 of well 230 have a profile 245. Profile 245 of sides 234 is noncircular with the interior angle 47 that, adjacent the discharge port 140, is smaller than other interior angles of the profile. In the example illustrated, interior angle 47 is smaller than all other interior angles of profile 245. In the example illustrated, the smallest interior angle 47, the angle between the opposing sides of the interior of well 230 on opposite transverse sides of discharge port 140, is an acute angle, less than 90 degrees. In contrast, remaining interior angles of well 230 are either curved or rounded and greater than 90°. As a result, during withdrawal or discharging of liquid from well 230, liquid is less likely to be held up or retained by capillary action between or within corners or acute angles. At the same time, during withdrawal or discharge of liquid from well 230, capillary action assists in wicking liquid towards discharge port 140.

Because sides 234 of well 230 have a profile 245 that inhibits retention of liquid in regions of the interior of well 230 away from discharge port 140 and which wick liquid towards discharge port 140, any liquid within well 230 is more likely to be more completely removed. As a result, the risk of contaminants resulting from inefficient removal of a liquid is reduced. The sloping of floor 36 further enhances withdrawal of liquid from the interior 241 of well 230.

In the example illustrated, profile 245 is illustrated as having a tear-drop shape, having a curved or rounded portion 251 opposite to discharge port 140 and two converging segments 252 extending from rounded portion 251 towards discharge port 140. As will be described hereafter, in other implementations, profile 245 may have other shapes. Although well 230 is illustrated as having sloped floor 36, in other implementations, well 230 may have a differently slope floor, such as floor 146 described above or other floor profiles. Although container 220 is illustrated as having a single well 230, in other implementations, container 220 may have multiple wells 230, such as a two dimensional array of such wells 230.

Figure 6:
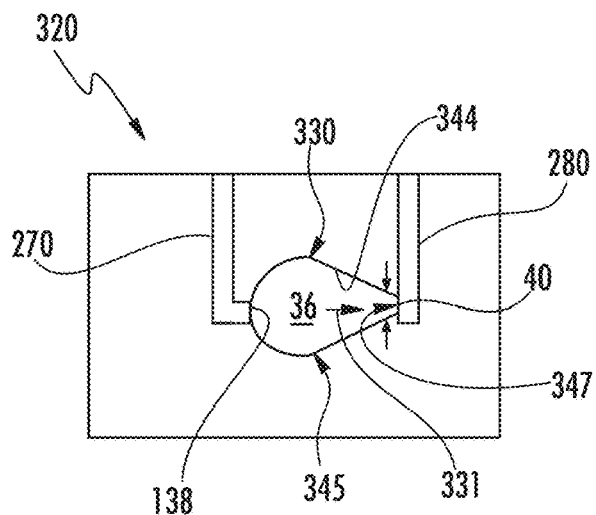
FIG. 6 is a top view of an example liquid directing sample container.

FIG. 6 is a top view of liquid directing sample container 320, which may be another implementation of container 220. Container 320 is similar to container 220 except that container 320 comprises well 330 in place of well 230. Well 330 has sides 344 having an alternative profile 345. Like well 230, well 330 has a floor 36 that slopes downwardly (from left to right in the figure as indicated by arrow 331) towards discharge port 40.

Like profile 245, the profile 345 of sides 344 is noncircular with an interior angle 347 that, adjacent to discharge port 40, is smaller than other interior angles of the profile 345. In the example illustrated, interior angle 347 is smaller than all other interior angles of profile 345. In the example illustrated, the smallest interior angle 347, the angle between the opposing transverse sides of the interior of well 330 on opposite transverse sides of discharge port 40, is an acute angle, less than 90 degrees. In contrast, remaining polygonal interior segments of sides 344 are separated by interior angles of greater than 90 degrees. As a result, during withdrawal or discharging of liquid from well 330, liquid is less likely to be held up or retained by capillary action between or within corners or acute angles. At the same time, during withdrawal or discharge of liquid from well 330, capillary action assists in wicking liquid towards discharge port 40.

Figure 7:
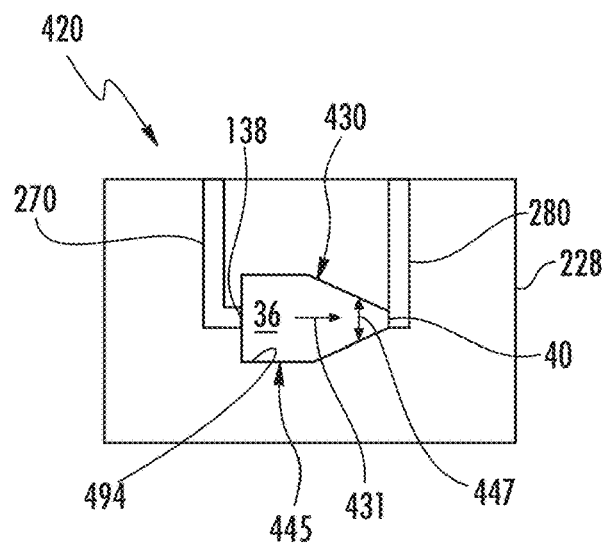
FIG. 7 is a top view of an example liquid directing sample container.

FIG. 7 is a top view of liquid directing sample container 420, which is another implementation of container 220. Container 420 is similar to container 220 except that container 420 comprises well 430 in place of well 230. Well 430 has sides 494 having an alternative profile 445. Like well 230, well 430 has a floor 36 that slopes downwardly (from left to right in the figure as indicated by arrow 431) towards discharge port 40.

Like profile 245, the profile 445 of sides 494 is noncircular with an interior angle 447 that, adjacent to discharge port 40, is smaller than all other interior angles of the profile 445. In the example illustrated, interior angle 447 is smaller than all other interior angles of profile 445. In the example illustrated, the smallest interior angle 447, the angle between the opposing transverse sides of the interior of well 430 on opposite transverse sides of discharge port 40, is an acute angle, less than 90 degrees. In contrast, remaining polygonal interior segments of sides 494 are separated by interior non-acute angles. As a result, during withdrawal or discharging of liquid from well 430, liquid is less likely to be held up or retained by capillary action between or within corners or acute angles. At the same time, during withdrawal or discharge of liquid from well 430, capillary action resulting from angle 447 assists in wicking liquid towards discharge port 40.

Figure 8:
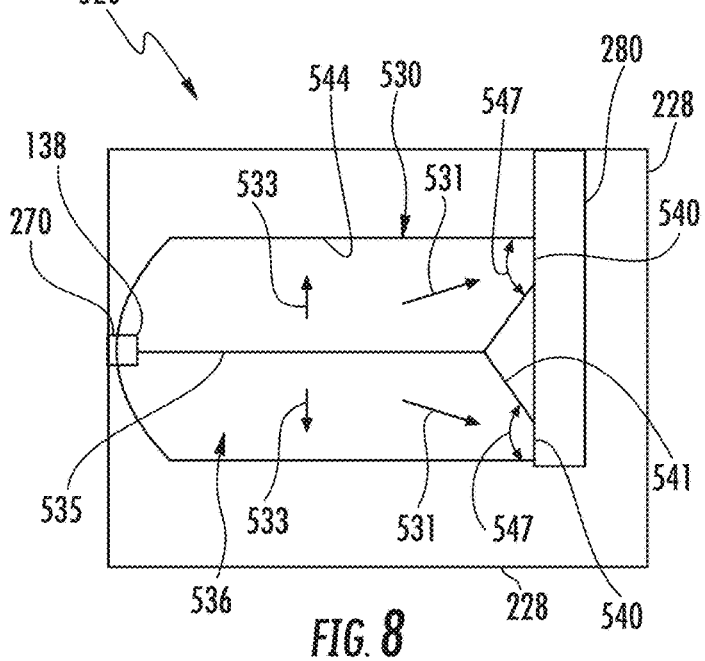
FIG. 8 is a top view of an example liquid directing sample container.

FIG. 8 is a top view of liquid directing sample container 520, which is another implementation of container 220. Container 520 is similar to container 220 except that container 520 comprises well 530 in place of well 230. Well 530 has sides 544 having a profile and includes two discharge ports or openings 540. Well 530 has a floor 536 that slopes downwardly (from left to right in the figure as indicated by arrows 531) towards discharge ports 540. In the example illustrated, floor 536 additionally slopes downwardly in the directions indicated by arrows 533, away from an elevated spine 535.

Like profile 245, the profile of sides 544 is noncircular with the interior angles 547 adjacent to discharge ports 540, separated by a divider 541. Interior angles 547 are smaller than all other interior angles of the profile. In the example illustrated, the interior angle 547, the angle between the opposing sides of the interior of well 530 on opposite horizontal sides of the respective discharge ports 540, is an acute angle, less than 90 degrees. In contrast, remaining polygonal interior segments of sides 544 are separated by interior non-acute angles. As a result, during withdrawal or discharging of liquid from well 530, liquid is less likely to be held up or retained by capillary action between or within corners or acute angles. At the same time, during withdrawal or discharge of liquid from well 530, capillary action resulting from each angle 547 assists in wicking liquid towards the respective discharge port 540.

Figure 9:
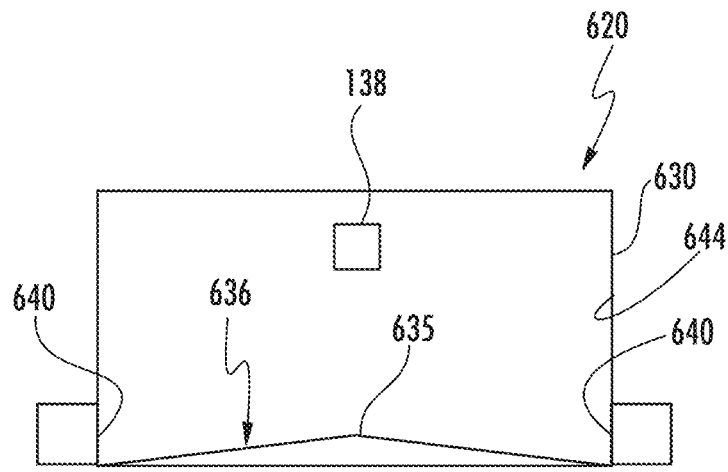
FIG. 9 is a sectional view of an example liquid directing sample container.
Figure 10:
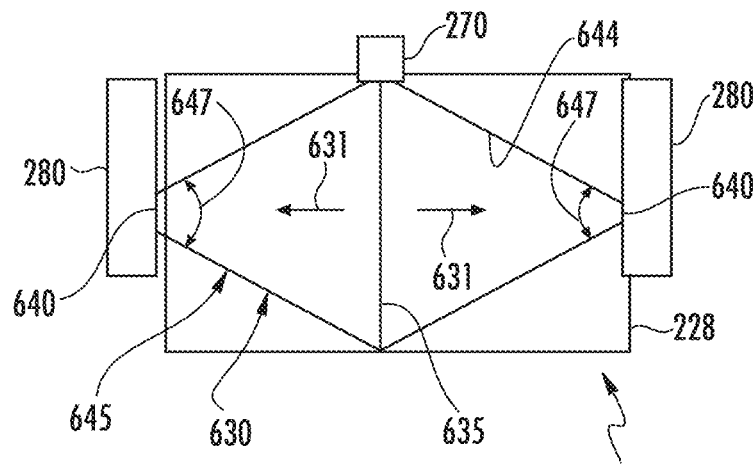
FIG. 10 is a top view of the example liquid directing sample container of FIG. 9.

FIGS. 9 and 10 illustrate liquid directing sample container 620, which is another implementation of container 220. Container 620 is similar to container 220 except that container 620 comprises well 630 in place of well 230. Well 630 has sides 644 having profile 645. Like well 530, well 630 has a floor 636 that slopes downwardly towards each of two discharge ports 640. In the example illustrated, discharge ports 640 are located on opposite sides or ends of well 630 with the floor 636 having an elevated spine 635 such that liquid within well 630 flows away from spine 635 in the directions indicated by arrows 631 towards discharge ports 640. In the example illustrated, inlet 138 extends through a side of well 630 (as shown in FIG. 9) above spine 635.

Like profile 245, the profile 645 of sides 644 is noncircular with the interior angles 647 adjacent to discharge ports 640. Angles 647 are smaller than remaining angles of profile 645. In the example illustrated, profile 645 is diamond-shaped with respective discharge ports 640 at opposite points of the diamond. In the example illustrated, the smallest interior angle 647, the angle between the opposing sides of the interior of well 630 on opposite horizontal sides of the respective discharge port 640, is an acute angle, less than 90 degrees. In contrast, remaining polygonal interior segments of sides 644 are separated by interior non-acute angles. As a result, during withdrawal or discharging of liquid from well 630, liquid is less likely to be held up or retained by capillary action between or within corners or acute angles. At the same time, during withdrawal or discharge of liquid from well 630, capillary action resulting from each angle 647 assists in wicking liquid towards the respective discharge port 640.

Figure 11:
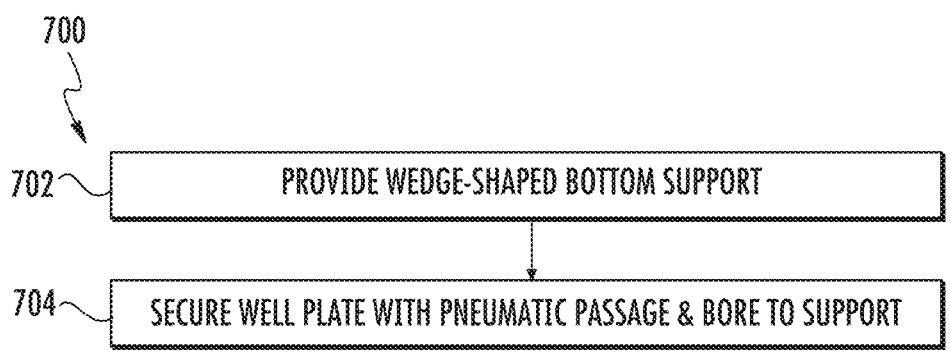
FIG. 11 is a flow diagram of an example method for forming an example liquid directing sample container.
Figure 12:
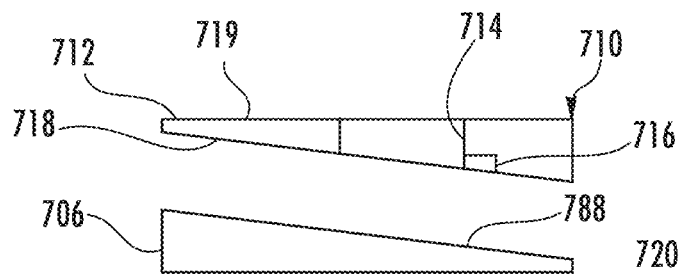
FIG. 12 is an exploded sectional view of an example liquid directing sample container.
Figure 13:
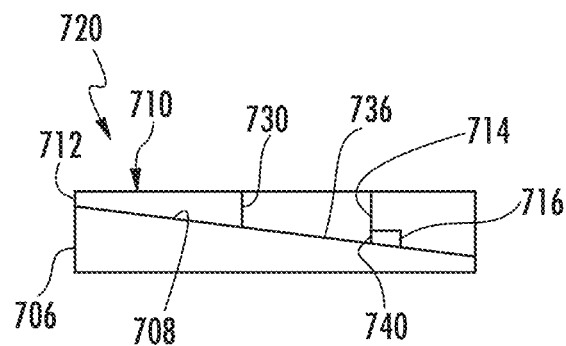
FIG. 13 is a sectional view of the assembled example liquid directing sample container of FIG. 12.

FIGS. 11-13 illustrate an example method 700 for forming an example liquid directing sample carrier 720 (shown assembled in FIG. 13). As indicated by block 702 in FIG. 11, a wedge-shaped bottom support 706 is provided. As shown by FIG. 12, the wedge-shaped bottom support 706 has a sloped upper surface 708, a first height at a first end and a second lower height at a second opposite end. In one implementation, bottom support 706 is formed from a polymer or multiple polymers. In another implementation, bottom support 706 is formed from a silicon-based material or other materials.

As indicated by block 704 in FIG. 11, a well plate, such as well plate 710 shown in FIG. 12, is secured to a top of the bottom support 706. As shown by FIG. 12, well plate 710 comprises body 712, bore 714 and passage 716. Body 712 has a lower surface 718 that is complementary to upper surface 708. Although illustrated as being wedge-shaped such that the upper surface 719 of body 712 is horizontal when assembled to support 706, in other implementations, body 712 may have other shapes such that the upper surface 719 is not level or horizontal after being secured to support 706.

Bore 714 extends completely through body 712. The sides of bore 714 serve as sides of the separately formed well. In one implementation, bore 714 is cylindrical. In another implementation, bore 714 may have a tear-drop shaped profile (when viewed from the top) similar to profile 245 illustrated above in FIG. 5, wherein the smallest angle of the profile is adjacent to the discharge port adjacent to passage 716. In another implementation, bore 714 may have profile 345 or profile 445 illustrated above in FIGS. 6 and 7, respectively, wherein the smallest angle is adjacent to the discharge port adjacent to passage 716. In yet other implementations, portions of upper surface 708 and bore 714 may cooperate to form wells such as shown in FIGS. 8, 9 and 10.

Passage 716 comprises a conduit through which fluid may be withdrawn or discharged from a well. In the example illustrated, passage 716 has a top and sides defined by body 712, wherein the floor of passage 716 is defined or provided by upper surface 708 of support 706. In other implementations, passage 716 may extend within body 712 such that the floor of passage 716 is further defined by body 712. Passage 716 opens into bore 714 through sides of bore 714. Passage 716 extends to a perimeter or outer surface of body 712 to facilitate connection to a waste destination and/or a pneumatic pump.

FIG. 13 illustrates well plate 710 secured to body support 706. The securement of well plate 710 to bottom support 706 may be provided by adhesives, welds, bonds, fasteners or other connection technologies. When assembled together, body 706 and well plate 710 cooperate to form well 730. Upper surface 708 of support 706 forms the floor of well 730. Well plate 710 is secured to the upper surface 708 of body support 706 so as to form a seal between plate 710 and support 706 about well 730. In the example illustrated, upper surface 708 of support 706 further forms the floor 736 of passage 716. Passage 716 opens into the formed well 730 to form a discharge port 740 at a lower end of floor 736 such that floor 736 slopes downward towards the discharge port 740.

Figure 14:
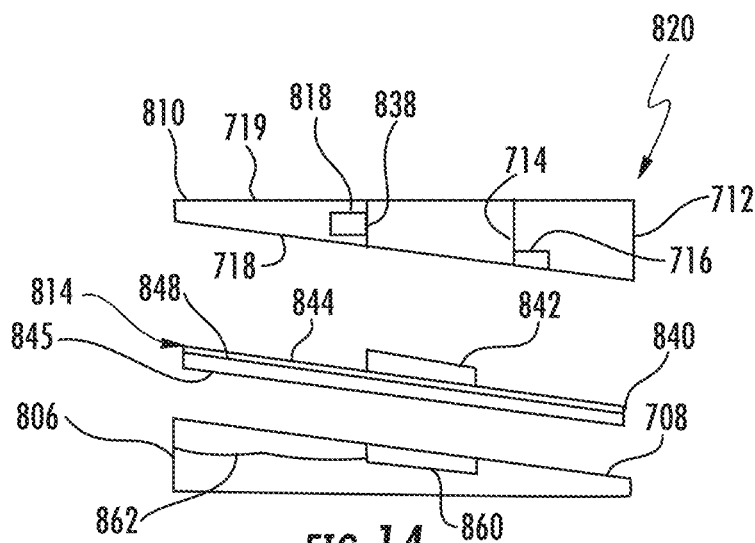
FIG. 14 is an exploded sectional view of an example liquid directing sample container.
Figure 15:
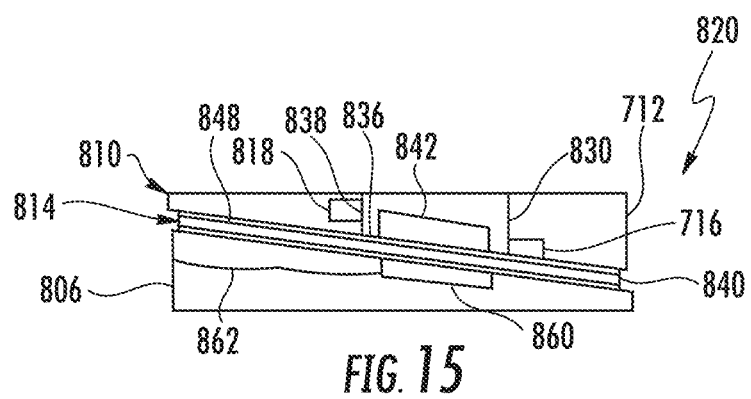
FIG. 15 is a sectional view of the assembled example liquid directing sample container of FIG. 14.

FIGS. 14 and 15 illustrate liquid directing sample container 820, which is another implementation of container 220. Container 820 contains a testing platform or stage and facilitates testing of an analyte sample. Container 820 is comprises bottom support 806, well plate 810 and sample sensing sheet 814.

Bottom support 806 is similar to bottom support 706 described above except that bottom support 806 additionally comprises heater 860 and electrical line 862. Heater 860 comprises a heating device formed along upper surface 708 of support 806 so as to emit heat which is conducted across sheet 810 to heat the contents of well 830. In one implementation, heater 860 comprises an electrically resistive heater that receives electrical power via electrical line 862, which is to be connected to an external electric power source. In other implementations, heater 760 and electrically conductive line 762 may be omitted.

Well plate 810 is similar to well plate 710 except that well plate 810 additionally comprises dispense passage 818. Those remaining components of well plate 810 which correspond to components of well plate 710 are numbered similarly. Dispense passage 818 comprises a fluid passage formed within body 712. Dispense passage 818 opens through the sides of bore 714 to form an inlet 838. Dispense passage 818 extends from bore 714 to a periphery of body 712 for releasable connection to a liquid source, such as a source of rinsing solvent. In the example illustrated, passage 818 is completely bounded on its top, bottom and sides by body 712. In other implementations, dispense passage 818 may extend along lower surface 718, wherein the floor passage 818 is supplied by the upper surface of sheet 814.

Sample sensing sheet 814 comprises substrate 840 and sensing structure 842. Substrate 840 supports sensing structure 842. In one implementation, substrate 840 comprises a flexible sheet, such as a thin polymer sheet, facilitating fabrication of sheet 814 with a roll-to-roll process. In other implementations, substrate 840 may be formed from substantially inflexible rigid material such as a rigid panel of silicon, a rigid polymer or other materials. In implementations where substrate 840 is sufficiently rigid to inhibit bending or flexing when being handled, bottom support 806 may be omitted.

Sensing structure 842 (schematically illustrated) comprises a structure that facilitates sensing of a sample. In one implementation, sensing structure 842 facilitates sensing of a sample using surface enhanced luminescence (SEL). In one implementation, sensing structure 842 facilitates sensing of a sample using surface enhanced Ramen spectroscopy (SERS). In one implementation, sensing structure 842 may comprise an island of an SEL structure, such as an SERS structure, that is sized and located so as to be received within bore 714 when sheet 814 is secured to an underside of well plate 810. In other implementations, sensing structure 842 may comprise other structures that facilitate sensing of a sample contained within well 830.

In implementations where sensing structure 842 comprises an SERS sensing structure, structure 842 may include a metal surface or structure, wherein interactions between the analyte and the metal surface cause an increase in the intensity of the Raman-scattered radiation. Such metal surfaces may include a roughened metal surface, such as periodic gratings. In another implementation, such metal surfaces may comprise assembled nanoparticles. In some implementations, such metal surfaces may comprise metal islands. In one implementation, such metal islands comprise flexible columnar supports such as pillars, needles, fingers, particles or wires. In some implementations, the flexible columnar structures may include a metal cap or head upon which an analyte may be deposited. In some implementations, such columnar structures are formed from materials and/or are dimensioned so as to bend or flex towards and away from one another in response to applied electric fields. In some implementations, the SERS structures are movable and are self-actuating, wherein such columnar structures bend or flex towards one another in response to microcapillary forces so as to self-organize, wherein such bending facilitates close spacing between the structures for greater scattered radiation intensity.

In some implementations, the columnar structures are electrically conductive such that the columnar structures and/or their metal caps or heads provide distinct charging points intensifying the generated electric field at distinct points to enhance attraction of the charged ions of the analyte to the columnar structures of structure 842. For example, in some implementations, the columnar structures are formed from an electrically conductive polymer such as Poly(3,4-ethylenedioxythiophene) or PEDOT (or sometimes PEDT), a conducting polymer based on 3,4-ethylenedioxythiophene or EDOT monomer. In one implementation, the SERS structures have a nanometer scale to facilitate nano-enhanced Raman spectroscopy (NERS). Such nano-scale NERS structures may increase the intensity of radiation scattered by the analyte adsorbed on such structures by a factor as high as $10^{16}$. In yet other implementations, such columnar structures may be formed from non-electrically conductive materials, such as non-electrically conductive polymers, or may be formed from metal materials, such as wire filaments or the like.

In implementations where bottom plate 806 omits heater 860 and electrical line 862, sensing sheet 814 may alternatively comprise heater 860 and electrical line 862. In such an implementation, heater 860 may be embedded within substrate 840 or formed below sensing structure 842 in a location so as to underlie bore 714 and the formed well 830.

As shown by FIG. 15, when bottom support 806, well plate 810 and sensing sheet 814 are assembled, sheet 814 is sandwiched between bottom support 806 and well plate 810 with upper surface 844 fixedly secured to surface 718 of well plate 810 and with lower surface 845 of sensing sheet 814 fixedly secured to upper surface 708 of bottom support 806. The securement of sensing sheet 814 to bottom support 806 and well plate 810 may be provided by adhesives, welds, bonds, fasteners or other connection technologies. Well plate 810 and sensing sheet 814 cooperate to form well 830, wherein sides 714 of bore 838 form the sides of wells 830 and wherein those portions of upper surface 844 of sensing sheet 814 underline bore 714 form the floor 836 of well 830. As further shown by FIG. 15, the island of the sensing structure 842 projects into and is received within bore 714 so as to extend along the bottom of well 830.

Portions of bottom surface 718 of well plate 810 about bore 714 are sealed against opposing portions of upper surface 844 of sensing sheet 814. As indicated by broken lines, in one implementation, the upper surface 844 of sensing sheet 814 comprises sealing structure 848 to provide a liquid tight seal between abutting portions of plate 810 and sheet 814 about well 830. In one implementation, the sealing structure 848 comprises an elastomeric or rubber-like gasket. In another implementation, the sealing structure 848 comprises an elastomer material or an adhesive. In one implementation, as shown by broken lines, the entirety of upper surface 844 is provided with sealing structure 848. In yet another implementation, sealing structure 848 may comprise a ring or other structure encircling the perimeter of bore 714. In yet other implementations, the opposing and abutting surfaces of plate 810 and sheet 814 may be joined in other fashions to one another to provide a liquid-tight seal about well 830. For example, the opposing and abutting surfaces of plate 810 and sheet 814 may alternatively be joined by welding, fusing, bonding or the like to provide a liquid tight seal about well 830. In yet other implementations, sealing structure 848 may alternatively be provided on the lower surface of plate 810 about bore 714 or may be provided as a separate layer sandwiched between plate 810 and sheet 814 about well 830.

Figure 16:
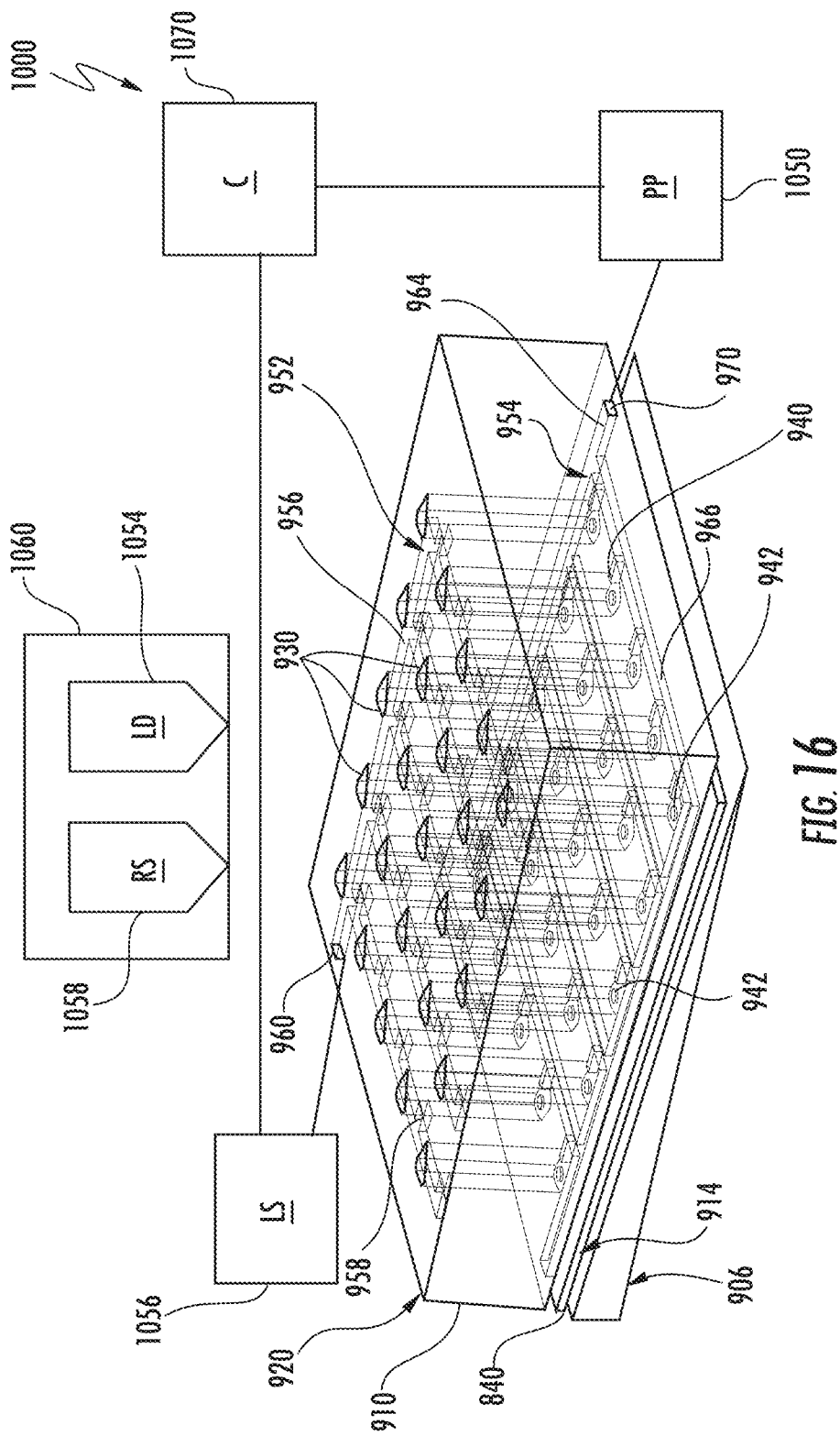
FIG. 16 is a top perspective view of an example sample preparation and sensing system comprising an example liquid directing sample container.

FIG. 16 illustrates an example liquid directing sample container 920 utilized as part of a sample preparation and sensing system 1000. Container 920 is similar to container 820 described above except that in the example illustrated, container 920 is releasably or removably connected to the remaining components of system 1000 so as to serve as a replaceable or interchangeable consumable or modular component for system 1000. Container 920 is similar to sample container 820 except that sample container 920 is specifically illustrated as comprising a two dimensional array or grid of wells 930 arranged in five rows and associated components and that each of wells 930 is specifically illustrated as having a tear-drop shaped profile, similar to the profile 245 shown in FIG. 5. Container 920 comprises bottom support 906, well plate 910 and sensing sheet 914.

Bottom support 906 is similar to bottom support 806 described above except that bottom support 906 comprises a two dimensional array or grid of heaters 860 (the first heater 860 in each row is illustrated for ease of illustration). The location of each of heaters 860 is aligned with and corresponds to one of the wells 930 formed by well plate 910 and sensor sheet 914. Each of the heaters 860 is connected to electrical line 862 (schematically shown in FIG. 15) extending to an electrical contact pad, allowing the heaters 860 to receive electrical current from an external power source. As described above, in some implementations, heaters 860 may alternatively be formed as part of sensor sheet 914.

Figure 17:
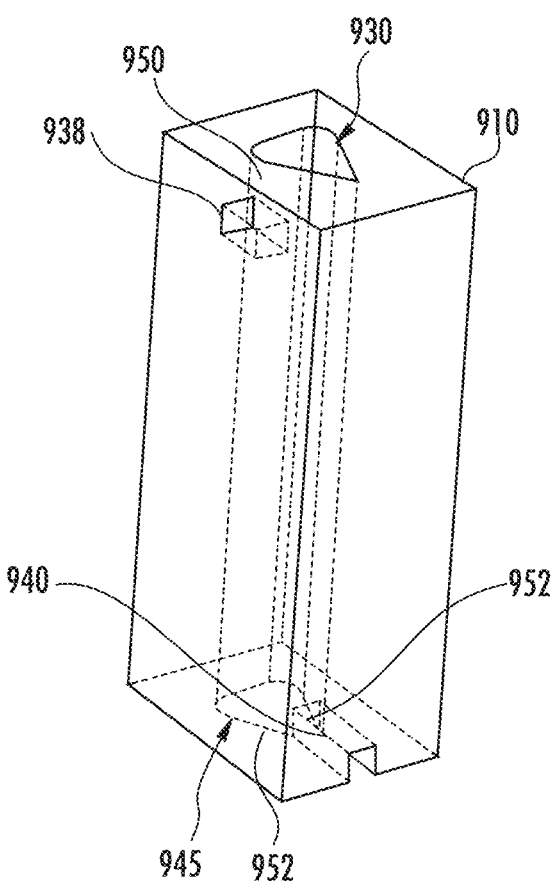
FIG. 17 is a bottom perspective view of a portion of the example liquid directing sample container of FIG. 16.

Well plate 910 is similar to well plate 810 described above except that well plate 910 comprises a two dimensional array of bores 714 (described above) with each bore 714 having a noncircular profile 945 (cross sectional shape when viewed from the top) and providing the sides of an individual well 930. FIG. 17 illustrates an individual well 930 of container 920. As shown by FIG. 17, similar to profile 245 in FIG. 5, the profile 945 of each bore 714 is noncircular with the smallest interior angle adjacent to discharge port 940. In the example illustrated, the smallest interior angle, the angle between the opposing sides of the interior of bore 714 on opposite transverse sides of discharge port 940, is an acute angle, less than 90 degrees. In contrast, remaining interior angles of well 930 are either curved or rounded and greater than 90 degrees. As a result, during withdrawal or discharging of liquid from well 930, liquid is less likely to be held up or retained by capillary action between or within corners or acute angles. At the same time, during withdrawal or discharge of liquid from well 930, capillary action assists in wicking liquid towards discharge port 940.

Because profile 945 inhibits retention of liquid in regions of the interior of well 930 away from discharge port 940 and wicks liquid towards discharge port 940, any liquid within well 930 is more likely to be more completely removed. As a result, the risk of contaminants resulting from inefficient removal of a liquid is reduced. The sloping of floor 836 further enhances withdrawal of liquid from the interior of each well 930.

In the example illustrated, profile 945 is illustrated as having a tear-drop shape, having a wider polygonal or curved portion 950 and two converging segments 952. The wider polygon or curved portion 950 extends adjacent to dispense port 938 while the converging segments 952 extend towards discharge port 940. As will be described hereafter, in other implementations, profile 945 may have other shapes.

As further shown by FIG. 16, well plate 924 further comprises dispense passage 952 and discharge passage 954. Dispense passage 952 comprises a main portion 956 and branches 958. Main portion 956 is connected each of branches 958 and terminates along an exterior of plate 910 at an exterior port 960. Branches 958 extend from main portion 956 and extend along each of the rows of wells 930, wherein each branch 958 is connected to the dispense port 938 of each of the wells 930 of the associated row.

Discharge passage 954 comprises a main portion 964 and branches 966. Main portion 964 is connected to each of branches 966 and terminates along an exterior of container 920 at an exterior port 970. Branches 966 extend from main portion 964 along each of the rows of wells 930, wherein each branch 966 is connected to the discharge port 940 of each of the wells 930 of the associated row.

Sensor sheet 914 is similar to sensor sheet 814 described above except that sheet 914 comprises a two dimensional array of spaced islands of sensor structures 942 supported by substrate 840. In the example illustrated, sensor structures 942 comprise SERS structures. In the example illustrated, substrate 840 supports five rows of spaced islands of sensor structures 942 which are located and sized to align with and be received within corresponding bores 917 of well plate 910 when container 920 is assembled. Because sheet 914 forms the floor of each of wells 930, the forming of well plate 910 may be facilitated in that well plate 910 includes bores that completely extends through well plate 924. Because sheet 914 is rigidified by bottom support 906, sheet 914 may be formed from a flexible material, having a reduced thickness to facilitate roll-to roll manufacture of sheet 914 and to facilitate the concurrent forming of multiple islands of SERS upon substrate 840. In one implementation, substrate 840 of sheet 914 is formed from a material such as polyethylene terephthalate and has a thickness of at least 0.01 mm and less than or equal to 0.5 mm. In one particular embodiment, sheet 914 has a thickness less than or equal to 500 um and in one implementation, less than or equal to 0.1 mm. In other implementations, substrate 840 of sheet 914 may be formed from other materials and may have other thicknesses.

Although container 920 is illustrated as comprising five rows of wells 930 with each row comprising five individual spaced wells 930, in other implementations, container 920 may include a greater or fewer of such rows as well as a greater or fewer of wells 930 within each row. Although arranged in a two dimensional grid, wells 930 may have other arrangements on container 920. Although illustrated as being rectangular, container 920 may have other shapes.

System 1000 facilitates preparation and sensing of multiple analyte samples in parallel. System 1000 comprises pneumatic pump (PP) 1050 (described above), liquid dispenser (LD) 1054 (described above), liquid supply 1056, Raman spectroscopy sensor 1058 and controller (C) 1070.

Liquid supply 1056 comprises a source of a liquid for use in preparing the sample and/or the SERS sensor. In the example illustrated, liquid supply 1056 comprises a source of a liquid rinsing solvent for preparing the SERS structure 942 for sensing by the Raman spectroscopy sensor 1058. In one implementation, liquid supply 1056 further comprises a pump to supply the liquid under pressure into passage 952 when container 920 is connected into system 1000 and in response to signals from controller 1070.

Raman spectroscopy sensor (RS) 1058 comprises a device that directs light, such as a laser beam of light, towards and onto sensor structure 942 of each of the wells 930 of container 920, and a device that focuses, gathers and detects and SERS spectra resulting from light scattering by the sample analyte on sensor structure 942. In one implementation, sensor 1058 comprises an infrared laser to emit a beam having a wavelength of 785 nm onto sensor structure 942 of each of wells 930. To direct the beam of light and focus the SERS spectra, resulting from scattering of the light by the sensor structure 942, sensor 1058 may include one or more optical components such as lenses and mirrors. The received SERS spectra is compared against previous identified spectrum fingerprints or signatures to identify characteristics of the sample analyte.

In one implementation, liquid dispenser 1054 and Raman spectroscopy sensor 1058 are supported and moved by a robot 1060 that selectively positions liquid dispenser 1054 and sensor 1058 with respect to each of wells 930 of container 920 in response to control signals from controller 1070. In yet other implementations, liquid dispenser 1054 and sensor 1058 may be moved and positioned by separate and independent robots.

Controller 1070 controls the operation of liquid supply 1056, heaters 860 and sensor 1058. Controller 1070 comprises electronic hardware, such as a processing unit to carry out instructions contained in a non-transitory computer-readable medium or memory. FIGS. 18-23 are sectional views illustrating controller 1070 preparing and sensing samples using container 920.

As illustrated by FIG. 18, controller 1070 (shown in FIG. 16) outputs control signals causing pneumatic pump 1050 to pressurize discharge passage 954 to inhibit entry of liquid from the wells 930 into discharge passage 954. While discharge passage 954 is pressurized, controller 1070 outputs control signals directing robot 1060 and liquid dispenser 1054 to dispense a sample of analyte 1100 into each of wells 930 so as to submerse each sensing structure 942. The dispensed sample of analyte 1100 submersing each sensing structure 942 is allowed to incubate for a predetermined period of time.

As illustrated by FIG. 19, after incubation, controller 1070 outputs control signals to pneumatic pump 1050 to create a vacuum within pneumatic passage 954, withdrawing, by vacuum, the samples of analyte 1100 from each of wells 930 through ports 940, leaving the incubated analyte 1100 on the SERS structures 942. As illustrated by FIG. 20, controller 1070 outputs control signals to pneumatic pump 1050 to once again pressurize discharge passage 954 to inhibit entry of liquid from the wells 930 into discharge passage 954. While discharge passage 954 is being pressurized, controller 1070 outputs control signals causing liquid supply 1056 to dispense rinsing solvent 1102, such as ethanol (EtOH), into each of wells 930 through dispense passage 952 and through the side ports 938. In the example illustrated, the rinsing solvent submerses each of sensing structures 942.

As illustrated by FIG. 21, after nano fingers of sensing structure 930 have closed in response to the application of the rinsing solvent 1102, controller 1070 outputs control signals to pneumatic pump 1050 to apply a negative pressure to discharge passage 954 to vacuum and withdraw the rinsing solvent 1102 through discharge passage 954. As illustrated by FIG. 22, to further evaporate any remaining rinsing solvent within each of wells 930, controller 1070 further outputs control signals to supply electrical current to heaters 860 which emit heat to each of wells 930. In the example illustrated, controller 1070 additionally outputs control signals directing a fan 1104 above container 920 to direct an inert gas, such as air, into each of wells 930 to further facilitate evaporation of any remaining rinsing solvent 1102. In some implementations, the air provided by fan 1104 is heated. In some implementations, controller 1070 additionally or alternatively outputs control signals further directing pneumatic pump 1050 to supply air into each of wells 930 through passage 954 to further assist in evaporation of any remaining rinsing solvent 1102.

After evaporation of the rinsing solvent, both the sample analyte 1100 and the sensing structures 942, comprising SERS structures, are ready for sensing and analysis. As illustrated by FIG. 23, controller 1070 outputs control signals causing robot 1060 (shown in FIG. 16) to sequentially position Raman sensor 1058 opposite each of wells 930 and to obtain SERS spectra from each sensing structures 942 within each well 930 for analysis.

FIGS. 24-29 illustrate an example use of an example liquid directing sample container 1120 to grow and monitor a culture of cells. Liquid directing sample container 1120 is similar to container 920 described above except that container 1120 omits sensor sheet 914 such that well plate 910 is secured directly on top of bottom support 906. As a result, 1120 comprises wells 1130 which are similar to wells 930 except that wells 1130 have floors provided by bottom support 906 that slope downwards towards discharge ports 940. In the example illustrated, each of wells 1130 may be emptied of liquid by pneumatic pump 1050 and discharge passage 954 (described with respect to container 920) and maybe filled with a liquid, such as a cell growth media, by a liquid source 1056 and dispense passage 956 (described with respect to container 920).

As illustrated by FIG. 24, a pneumatic pump, such a pneumatic pump 1050, is directed by a controller, such as controller 1070, to pressurize discharge passage 954 to inhibit entry of liquid from the wells 1130 into discharge passage 954. While discharge passage 954 is pressurized, liquid dispenser 1054 is directed by the controller 1070 to dispense cells 1200 into each of wells 1130.

As illustrated by FIG. 25, while discharge passage 954 is being pressurized, a liquid supply, such as liquid supply 1056, is directed to a cell growth media 1204, such as Lysogeny broth, balanced salt solutions (e.g. phosphate buffered saline, Earls balanced salt solution, Hank's balanced salt solution and the like), basal media (e.g. a modified Eagle medium), complex media (e.g., a Roswell Park Memorial Institute (RPMI) medium), serum free media and insect cells (designed for use with sf9 insect cells) into each of wells 1130 through dispense passage 952 and through the side ports 938. In the example illustrated, the growth media submerses each of cultures of cells 1200.

As illustrated by FIG. 26, after the growth media 1204 has been sufficiently exhausted or consumed by cells 1200, the pneumatic pump 1050 is activated to apply a negative pressure to discharge passage 954 to vacuum and withdraw the used cell growth media 1202 through discharge passage 954. As illustrated by FIG. 27, while discharge passage 954 is once again pressurized, a liquid supply, such as liquid supply 1056, is directed to add new cell growth media 1204, such as Lysogeny broth, balanced salt solutions, basal media, complex media, serum free media and insect cells, into each of wells 1130 through dispense passage 952 and through the side ports 938. In the example illustrated, the new growth media submerses each of cultures of cells 1200. As illustrated by FIG. 27, during growth of cells, heaters 860 are further controlled to control the temperatures of each of wells 1130 to enhance cell growth. As indicated by FIG. 28, the steps illustrated in FIGS. 26 and 27 are repeated to achieve a predetermined amount of cell growth. As illustrated by FIG. 29, the cells within each of wells 1130 may be periodically monitored by an overhead camera or other imaging device 1214.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. An apparatus comprising:
   a liquid directing sample container comprising:
      a well comprising:
         sides having a non-circular profile, the non-circular profile having interior angles, at a first target location and a second target location within the well, that are smaller than other interior angles of the non-circular profile to wick liquid towards the first target location and towards the second target location, wherein the sides of the well have a profile having a first corner adjacent the first target location and a second corner adjacent the second target location; and
         a floor having first and second portions, wherein the first portion is sloped to direct liquid towards the first corner and a first discharge port adjacent the first target location and the second portion is sloped towards the second corner and a second discharge port adjacent the second target location.

2. The apparatus of claim 1, further comprising a plate in which the well is formed, wherein the liquid directing sample container further comprises a pneumatic passage within the plate and connected to the first discharge port and the second discharge port of the well.

3. The apparatus of claim 2, further comprising a pneumatic pump connected to the pneumatic passage to create a vacuum within the pneumatic passage.

4. The apparatus of claim 1, wherein the sides of the well have a curved side opposite the first target location and the second target location.

5. The apparatus of claim 1, wherein the sides of the well have wide portions and narrow portions, the narrow portions being adjacent the first target location and the second target location.

6. The apparatus of claim 1, wherein the apparatus further comprises:
   a second well, the second well comprising:
      a third discharge port;
      second sides having a second non-circular profile, the second non-circular profile of the second sides having an interior angle, at a third target location within the second well, that is smaller than all other interior angles of the profile of the second sides to wick liquid towards the third discharge port; and
      a floor, wherein the floor is sloped downward to direct liquid towards the third discharge port,
   the first discharge port of the well being at a first height and the third discharge port of the second well being at a second height below the first height.

7. The apparatus of claim 6, wherein the liquid directing sample container further comprises a pneumatic passage within a plate and is connected to the first discharge port, the second discharge port, and the third discharge port.

8. The apparatus of claim 1, wherein the well further comprises an inlet through which the liquid is dispensed into an interior of the well.

9. The apparatus of claim 1, further comprising a surface enhanced Raman spectroscopy structure extending from the floor within the well.

10. An apparatus comprising:
    a liquid directing sample container comprising:
       a plate;
       a well formed in the plate, the well comprising:
          sides;
          a floor having first and second portions;
          a first discharge port adjacent a first target location; and
          a second discharge port adjacent a second target location, wherein the sides of the well have a non-circular profile having interior angles at the first target location and the second target location that are smaller than other interior angles of the non-circular profile, wherein the sides of the well have a profile having a first corner adjacent the first target location and a second corner adjacent the second target location, and wherein the first portion is sloped to direct liquid towards the first corner and the first discharge port adjacent the first target location and the second portion is sloped towards the second corner and the second discharge port adjacent the second target location.

11. The apparatus of claim 10, wherein the sides of the well have a curved side opposite the first discharge port and the second discharge port.

12. A method for forming a sample container, the method comprising:
    providing a wedge-shaped bottom support having a first end having a first height and a second end having a second height less than the first height;
    securing a well plate to an upper surface of the wedge-shaped bottom support, the well plate comprising:
       a pneumatic passage; and
       bores extending completely through the well plate, each of the bores having a discharge port on a side of the bore proximate the second end of the bottom support and sides having a non-circular profile having an interior angle, at the discharge port, that is smaller than other interior angles of the profile.

13. The method of claim 12, further comprising sandwiching a sheet, from which islands of surface enhanced surface enhanced luminescence (SEL) structures rise, between the wedge-shaped bottom support and the well plate with the islands of the SEL structures projecting into the bores.

14. The apparatus of claim 10, wherein the apparatus further comprises:
    a second well, the second well comprising:
       a third discharge port;
       second sides having a second non-circular profile, the second non-circular profile of the second sides having an interior angle, at a third target location within the second well, that is smaller than all other interior angles of the profile of the second sides to wick liquid towards the third discharge port; and
       a floor, wherein the floor is sloped downward to direct liquid towards the third discharge port,
    the first discharge port of the well being at a first height and the third discharge port of the second well being at a second height below the first height.

15. The apparatus of claim 14, wherein the liquid directing sample container further comprises a pneumatic passage within a plate and is connected to the first discharge port, the second discharge port, and the third discharge port.

\* \* \* \* \*